(12) United States Patent
Zergiebel et al.

(10) Patent No.: US 9,839,424 B2
(45) Date of Patent: Dec. 12, 2017

(54) ELECTROMECHANICAL SURGICAL ASSEMBLY

(71) Applicant: Covidien LP, Mansfield, MA (US)

(72) Inventors: Earl M. Zergiebel, Guilford, CT (US); Matthew Chowaniec, Middletown, CT (US)

(73) Assignee: Covidien LP, Mansfield, MA (US)

( * ) Notice: Subject to any disclaimer, the term of this patent is extended or adjusted under 35 U.S.C. 154(b) by 429 days.

(21) Appl. No.: 14/559,046

(22) Filed: Dec. 3, 2014

(65) Prior Publication Data

US 2015/0201931 A1    Jul. 23, 2015

Related U.S. Application Data

(60) Provisional application No. 61/928,479, filed on Jan. 17, 2014.

(51) Int. Cl.
    *A61B 17/068*      (2006.01)
    *A61B 18/08*      (2006.01)
    (Continued)

(52) U.S. Cl.
    CPC ...... *A61B 17/068* (2013.01); *A61B 17/07207* (2013.01); *A61B 18/085* (2013.01); *A61B 18/1442* (2013.01); *A61B 18/1445* (2013.01); *A61B 90/40* (2016.02); *A61B 2017/0046* (2013.01); *A61B 2017/00398* (2013.01); *A61B 2017/00477* (2013.01); *A61B 2017/00526* (2013.01); *A61B 2017/00734* (2013.01); *A61B 2017/00889* (2013.01); *A61B 2018/00172* (2013.01); *A61B 2018/00178* (2013.01);
    (Continued)

(58) Field of Classification Search
    CPC ....... A61B 17/04; A61B 17/32; A61B 17/068; A61B 17/072; A61B 17/85; A61C 5/14; A61F 5/56
    USPC ................................ 227/175.1, 176.1, 180.1
    See application file for complete search history.

(56) References Cited

U.S. PATENT DOCUMENTS 2,777,340 A    1/1957   Hettwer et al.
2,957,353 A   10/1960   Babacz
(Continued)

FOREIGN PATENT DOCUMENTS

CN         101856251 A    10/2010
DE    102012013242 A1    1/2014
(Continued)

OTHER PUBLICATIONS

European Search Report for EP 14199658.7 dated Jun. 12, 2015.
(Continued)

*Primary Examiner* — Nathaniel Chukwurah

(57) ABSTRACT

An electromechanical surgical assembly includes a surgical device, an adapter, and a filter. The surgical device includes a connecting portion having a distal facing recess including an electrical plug. The adapter includes a proximal facing cap configured to mate with the recess of the surgical device, the proximal facing cap including an electronic assembly including a plurality of electrical contact pins configured for electrical connection with the electrical plug. The filter is removably positioned within the recess of the surgical device. The plurality of electrical contact pins extend through the filter when the adapter is connected to the surgical device.

23 Claims, 3 Drawing Sheets

(51) Int. Cl.
*A61B 18/14* (2006.01)
*A61B 17/072* (2006.01)
*A61B 17/00* (2006.01)
*A61B 18/00* (2006.01)
*A61B 90/40* (2016.01)
*A61B 90/00* (2016.01)

(52) U.S. Cl.
CPC .............. *A61B 2090/0813* (2016.02); *A61B 2560/0443* (2013.01)

(56) References Cited

U.S. PATENT DOCUMENTS

| | | | |
|---|---|---|---|
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,413,573 A | 5/1995 | Koivukangas | |
| 5,427,087 A | 6/1995 | Ito et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,632,432 A | 5/1997 | Schulze et al. | |
| 5,647,526 A | 7/1997 | Green et al. | |
| 5,653,374 A | 8/1997 | Young et al. | |
| 5,658,300 A | 8/1997 | Bito et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,714,343 A * | 2/1998 | Tuompo .................. | C12Q 1/04 435/29 |
| 5,762,603 A | 6/1998 | Thompson | |
| 5,766,169 A | 6/1998 | Fritzsch et al. | |
| 5,779,130 A | 7/1998 | Alesi et al. | |
| 5,782,396 A | 7/1998 | Mastri et al. | |
| 5,782,397 A | 7/1998 | Koukline | |
| 5,797,536 A | 8/1998 | Smith et al. | |
| 5,820,009 A | 10/1998 | Melling et al. | |
| 5,863,159 A | 1/1999 | Lasko | |
| 5,865,361 A | 2/1999 | Milliman et al. | |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,171,316 B1 | 1/2001 | Kovac et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,330,965 B1 | 12/2001 | Milliman et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,997,931 B2 | 2/2006 | Sauer et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,114,500 B2 | 10/2006 | Bonutti |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |

(56) References Cited

U.S. PATENT DOCUMENTS

| | | |
|---|---|---|
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,717,117 B2 | 5/2010 | Duarte |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,202,278 B2 | 6/2012 | Orban, III et al. |
| 8,220,367 B2 | 7/2012 | Hsu |
| 8,235,273 B2 | 8/2012 | Olson et al. |
| 8,241,322 B2 | 8/2012 | Whitman et al. |
| 8,245,898 B2 | 8/2012 | Smith et al. |
| 8,272,554 B2 | 9/2012 | Whitman et al. |
| 8,286,637 B2 | 10/2012 | Kaska |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2003/0216723 A1 | 11/2003 | Shinmura et al. |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0264921 A1 | 11/2006 | Deutsch et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0161949 A1* | 7/2007 | Knox .............. A61M 25/0017 604/93.01 |

(56) References Cited

U.S. PATENT DOCUMENTS

| | | |
|---|---|---|
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0105750 A1 | 4/2009 | Price et al. |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2009/0314821 A1 | 12/2009 | Racenet |
| 2010/0069942 A1 | 3/2010 | Shelton, IV |
| 2010/0193568 A1 | 8/2010 | Scheib et al. |
| 2010/0198220 A1 | 8/2010 | Boudreaux et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1* | 10/2012 | Zemlok ............. A61B 17/072 606/1 |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0087156 A1 | 4/2013 | Sloth et al. |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0144970 A1 | 5/2014 | Aranyi et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| EP | 1674045 A2 | 6/2006 |
| EP | 1759652 A2 | 3/2007 |
| EP | 1908412 A2 | 4/2008 |
| EP | 1917929 A1 | 5/2008 |
| EP | 1952769 A2 | 8/2008 |
| EP | 2090247 A1 | 8/2009 |
| EP | 2245994 A1 | 11/2010 |
| EP | 2377472 A1 | 10/2011 |
| EP | 2668910 A2 | 12/2013 |
| EP | 2815705 A1 | 12/2014 |
| FR | 2861574 A1 | 5/2005 |
| KR | 20120022521 A | 3/2012 |
| WO | 2009/039506 A1 | 3/2009 |
| WO | 2009/039510 A1 | 3/2009 |

OTHER PUBLICATIONS

Extended European Search Report corresponding to International Application No. EP 15 15 1076.5 dated Apr. 22, 2015.

Japanese Office Action corresponding to International Application No. JP 2011-084092 dated Jan. 14, 2016.

(56) References Cited

OTHER PUBLICATIONS

Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
U.S. Appl. No. 61/911,774, now U.S. Appl. No. 14/513,283, filed Oct. 14, 2014.

\* cited by examiner

ELECTROMECHANICAL SURGICAL ASSEMBLY

CROSS-REFERENCE TO RELATED APPLICATIONS

This application claims the benefit of and priority to U.S. Provisional Patent Application No. 61/928,479, filed Jan. 17, 2014, the entire disclosure of which is incorporated by reference herein.

BACKGROUND

1. Technical Field

The present disclosure relates to electromechanical surgical assembly systems. More specifically, the present disclosure relates to electromechanical surgical assembly systems including an electromechanical surgical device having a removable filter for preventing contamination of the internal components of the electromechanical surgical device when an adapter and/or surgical loading unit is electrically and/or mechanically interconnected with the electromechanical surgical device.

2. Background of Related Art

A number of surgical device manufacturers have developed product lines with proprietary drive systems for operating and/or manipulating electromechanical surgical devices. In many instances the electromechanical surgical devices include a handle assembly, which is reusable, and disposable loading units and/or single use loading units or the like that are selectively connected to the handle assembly prior to use and then disconnected from the handle assembly following use in order to be disposed of or in some instances sterilized for re-use.

In certain instances, an adapter is used to interconnect an electromechanical surgical device with any one of a number of surgical loading units to establish a mechanical and/or electrical connection therebetween. The adapter, or different adapters, may be attached and detached to/from an electromechanical surgical instrument during a surgical procedure. In such instances, the internal components of the electromechanical surgical device can become contaminated during attachment of an adapter that has been previously used during a surgical procedure.

Accordingly, it would be beneficial to have an electromechanical surgical device including a protective barrier for sterile connection between the electrical components of an adapter and the electromechanical surgical device.

SUMMARY

The present disclosure is directed to improvements in electromechanical surgical assemblies. In accordance with an aspect of the present disclosure, an electromechanical surgical assembly includes a surgical device, an adapter, and a filter. The surgical device includes a connecting portion having a distal facing recess including an electrical plug. The adapter includes a proximal facing cap configured to mate with the distal facing recess of the surgical device, the proximal facing cap including an electronic assembly including a plurality of electrical contact pins configured for electrical connection with the electrical plug. The filter is removable positioned within the distal facing recess of the surgical device. The plurality of electrical contact pins extend through the filter when the adapter is connected to the surgical device.

The filter includes at least one layer of material selected from the group consisting of fabrics, foams, elastomers, thermoplastics, gels, and combinations thereof. In embodiments, the filter is a composite of two or more layers of material. The filter includes a therapeutic agent. In embodiments, the therapeutic agent is selected from the group consisting of antimicrobials, antibacterials, antiseptics, astringents, disinfectants, and combinations thereof. In certain embodiments, the filter includes slits or apertures.

In some embodiments, the filter may have a shape that is complementary to a shape of the entire recess, while in some other embodiments, the filter may have a shape that is complementary to a shape of a portion of the recess. The filter may be self-supporting or may be attached to a base plate mounted within the recess.

In accordance with another aspect of the present disclosure, an electromechanical surgical device that is interconnectable with an adapter for selectively interconnecting a surgical loading unit with the surgical device includes a handle housing, a connecting portion extending distally from the handle housing, the connecting portion including at least one rotatable drive shaft and an electrical plug defined within a distal facing recess, and a filter disposed within the recess distal to the at least one rotatable drive shaft and the electrical plug. The filter is configured to prevent contaminants from communicating with the electrical plug.

The filter includes at least one layer of material selected from the group consisting of fabrics, foams, elastomers, thermoplastics, gels, and combinations thereof. In embodiments, the filter is a composite of two or more layers of material. The filter includes a therapeutic agent. In embodiments, the therapeutic agent is selected from the group consisting of antimicrobials, antibacterials, antiseptics, astringents, disinfectants, and combinations thereof. In certain embodiments, the filter includes slits or apertures.

In some embodiments, the filter may have a shape that is complementary to a shape of the entire recess, while in some other embodiments, the filter may have a shape that is complementary to a shape of a portion of the recess. The filter may be self-supporting or may be attached to a base plate mounted within the recess.

In accordance with yet another aspect of the present disclosure, a method of using an electromechanical surgical assembly includes positioning a filter within a distal facing recess of a connecting portion of a surgical device and connecting an adapter to the surgical device. The distal facing recess includes an electrical plug, and the adapter includes a proximal facing cap configured to mate with the recess of the surgical device. The proximal facing cap includes an electronic assembly including a plurality of electrical contact pins configured to extend through the filter for electrical connection with the electrical plug. In certain embodiments, positioning the filter includes attaching the filter to a base plate mounted within the recess. In some embodiments, the filter is moistened with a therapeutic agent prior to positioning the filter within the recess of the surgical device.

The method may further include disconnecting the adapter from the surgical device and removing the filter from the recess of the surgical device. In embodiments, a new filter may be positioned within the distal facing recess of the connecting portion of the surgical device and the adapter, or a different adapter, may be attached to the surgical device.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
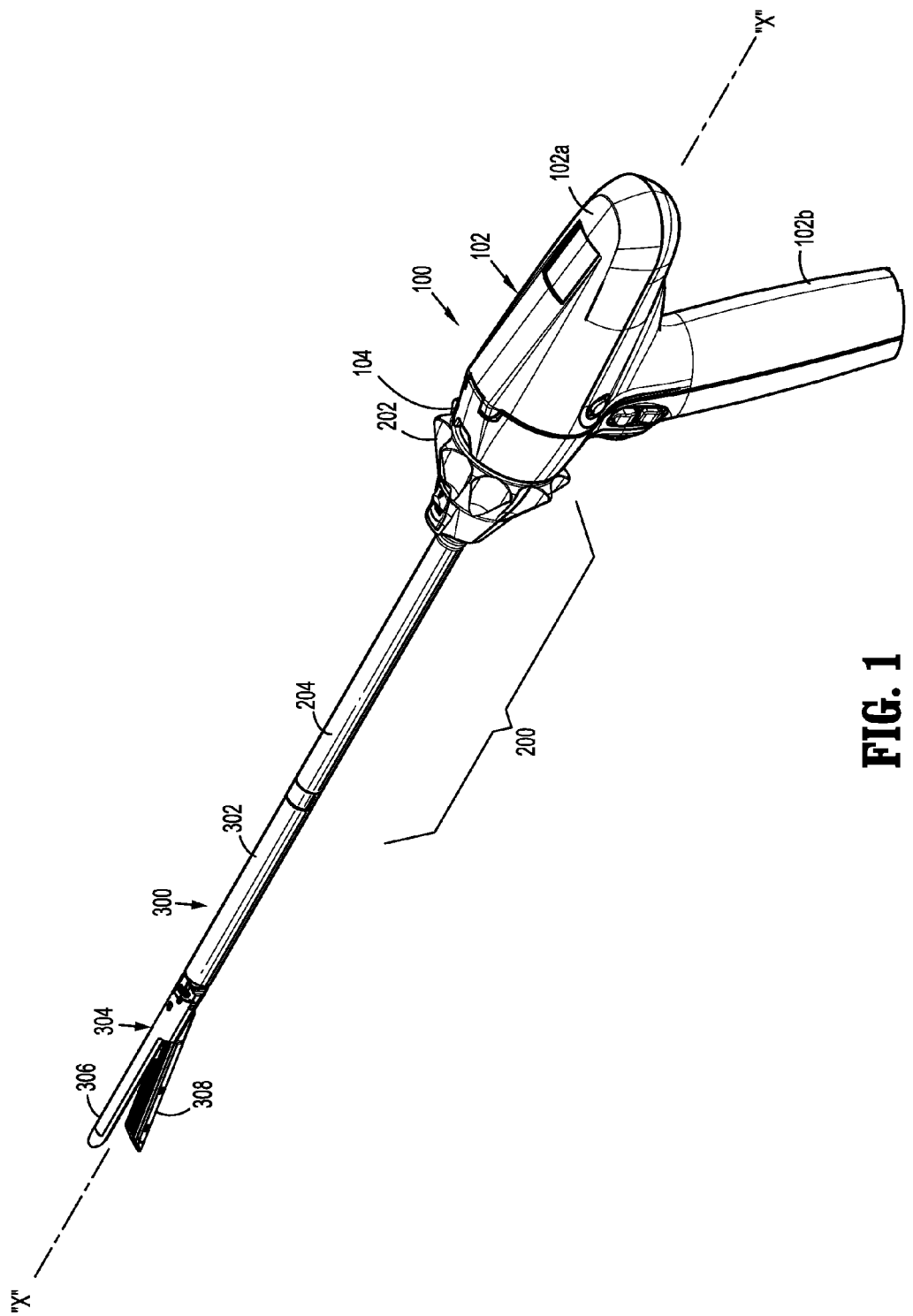
FIG. 1 is a perspective view of an electromechanical surgical assembly system in accordance with an illustrative embodiment of the present disclosure including an adapter interconnected between an electromechanical surgical device and an end effector.

Embodiments of the presently disclosed electromechanical surgical assemblies including surgical devices, adapters, and end effectors are described in detail with reference to the drawings, in which like reference numerals designate identical or corresponding elements in each of the several views. As used herein, the term "distal" refers to a portion of a structure that is farther from a clinician, while the term "proximal" refers to a portion of a structure that is closer to a clinician. As used herein, the term "clinician" refers to a doctor, nurse or other care provider and may include support personnel.

A surgical device, in accordance with an embodiment of the present disclosure, is generally designated as 100, and is in the form of a powered handheld electromechanical instrument or device configured for selective attachment thereto of a plurality of different end effectors that are each configured for actuation and manipulation by the powered handheld electromechanical surgical device. For the purposes of the present disclosure, the end effectors will be described in terms of surgical loading units; however, the disclosed electromechanical surgical assemblies can be used with a variety of end effectors within the purview of those skilled in the art, such as, for example, clamping jaws and cutting tools.

As illustrated in FIG. 1, an electromechanical surgical assembly 1 includes a surgical device 100 configured for selective connection with an adapter 200, and, in turn, the adapter 200 is configured for selective connection with a loading unit 300 (e.g., multiple- or single-use loading units, etc.). The surgical device 100 includes a handle housing 102 including a circuit board (not shown) and a drive mechanism (not shown) situated therein. The circuit board is configured to control the various operations of the surgical device 100. The handle housing 102 defines a cavity therein (not shown) for selective removable receipt of a rechargeable battery (not shown). The battery is configured to supply power to any of the electrical components of the surgical device 100.

The handle housing 102 includes an upper housing portion 102a which houses various components of the surgical device 100, and a lower hand grip portion 102b extending from the upper housing portion 102a. The lower hand grip portion 102b may be disposed distally of a proximal-most end of the upper housing portion 102a. The location of the lower hand grip portion 102b relative to the upper housing portion 102a is selected to balance a weight of a surgical device 100 that is connected to or supporting an adapter 200 and/or a loading unit 300.

The handle housing 102 provides a housing in which the drive mechanism is situated and supports a plurality of finger-actuated control buttons, rocker devices, and the like for activating various functions of the surgical device 100. The drive mechanism is configured to drive shafts and/or gear components in order to perform the various operations of the surgical device 100. In particular, the drive mechanism is configured to drive shafts and/or gear components in order to selectively move a tool assembly 304 of the loading unit 300 relative to a proximal body portion 302 of the loading unit 300, to rotate the loading unit 300 about a longitudinal axis "X" relative to the handle housing 102, and to move/approximate an anvil assembly 306 and a cartridge assembly 308 of the loading unit 300 relative to one another, and/or to fire a stapling and cutting cartridge within cartridge assembly 308 of the loading unit 300.

Figure 2:
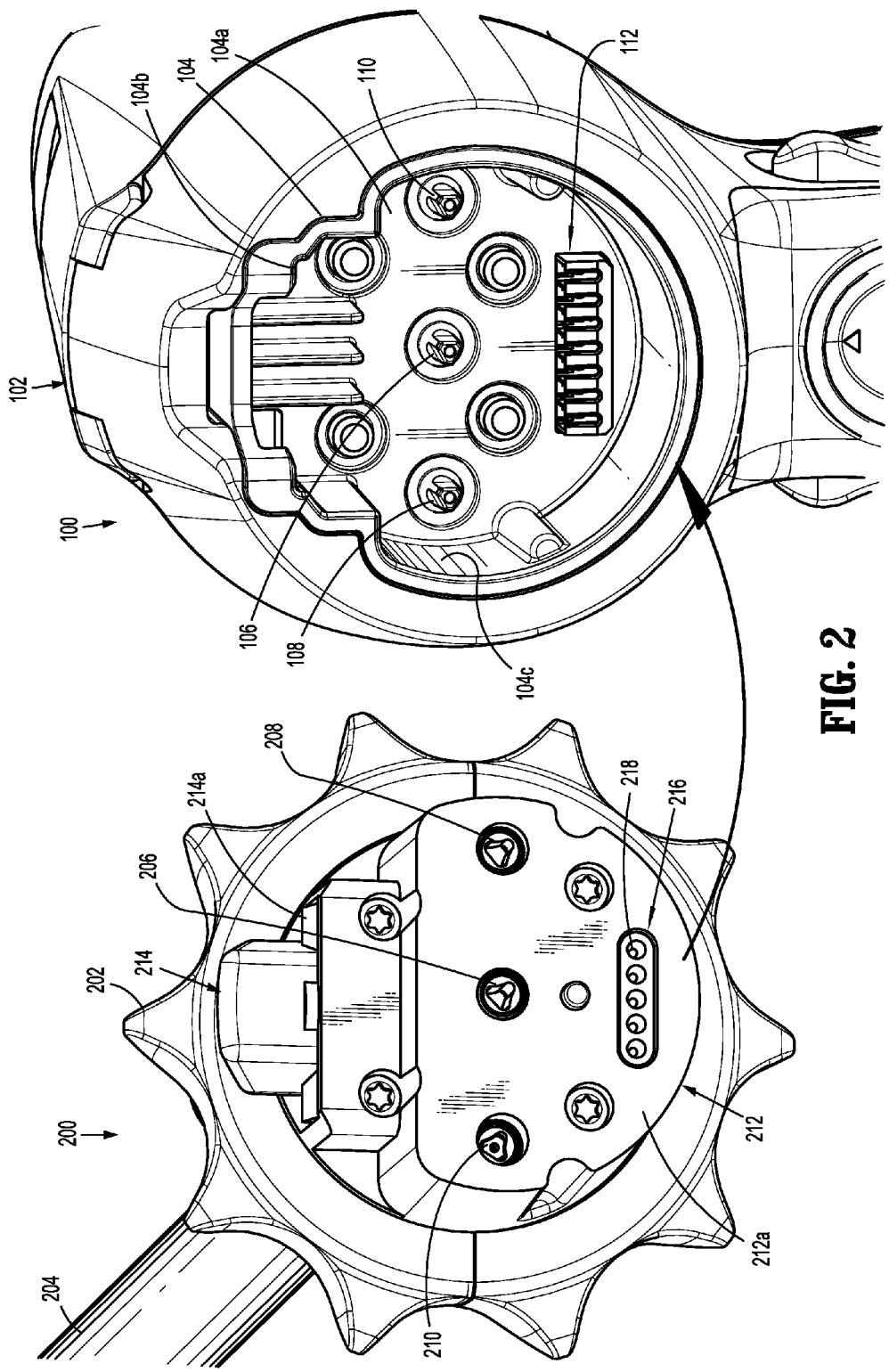
FIG. 2 is a perspective view illustrating an attachment of a proximal end of the adapter to a distal end of the electromechanical surgical device of FIG. 1.

As shown in FIG. 2, in conjunction with FIG. 1, the handle housing 102 defines a connecting portion 104 configured to accept a corresponding drive coupling assembly 212 of adapter 200. Specifically, connecting portion 104 of surgical device 100 has a distal facing recess 104a that receives a proximal facing cap 212a of the drive coupling assembly 212 of the adapter 200 when the adapter 200 is mated to the surgical device 100. The connecting portion 104 houses three rotatable drive connectors 106, 108, 110 which are arranged in a common plane or line with one another.

When the adapter 200 is mated to surgical device 100, each of the rotatable drive connectors 106, 108, 110 of the surgical device 100 couples with a corresponding rotatable connector sleeve 206, 208, 210 of the adapter 200. In this regard, the interface between the corresponding first drive connector 106 and the first connector sleeve 206, the interface between the corresponding second drive connector 108 and the second connector sleeve 208, and the interface between the corresponding third drive connector 110 and the third connector sleeve 210 are keyed such that rotation of each of the drive connectors 106, 108, 110 of the surgical device 100 causes a corresponding rotation of the corresponding connector sleeve 206, 208, 210 of the adapter 200.

The mating of the drive connectors 106, 108, 110 of the surgical device 100 with the connector sleeves 206, 208, 210 of the adapter 200 allows rotational forces to be independently transmitted via each of the three respective connector interfaces. The drive connectors 106, 108, 110 of the surgical device 100 are configured to be independently rotated by the drive mechanism of the surgical device 100. In this regard, a function selection module (not shown) of the drive mechanism selects which drive connector or connectors 106, 108, 110 of the surgical device 100 is to be driven by the motor of the surgical device 100.

Since each of the drive connectors 106, 108, 110 of the surgical device 100 has a keyed and/or substantially non-rotatable interface with the respective connector sleeves 206, 208, 210 of the adapter 200, when the adapter 200 is coupled to the surgical device 100, rotational force(s) are selectively transferred from the drive mechanism of the surgical device 100 to the adapter 200.

The selective rotation of the drive connector(s) 106, 108, 110 of the surgical device 100 allows the surgical device 100 to selectively actuate different functions of the loading unit 300. For example, selective and independent rotation of the first drive connector 106 of the surgical device 100 corresponds to the selective and independent opening and closing of the tool assembly 304 of the loading unit 300, and driving of a stapling/cutting component of the tool assembly 304 of the loading unit 300. As an additional example, the selective and independent rotation of the second drive connector 108 of the surgical device 100 corresponds to the selective and independent articulation of the tool assembly 304 of the loading unit 300 transverse to longitudinal axis "X". Additionally, for instance, the selective and independent rotation of the third drive connector 110 of the surgical device 100 corresponds to the selective and independent rotation of the loading unit 300 about longitudinal axis "X" relative to the handle housing 102 of the surgical device 100.

The adapter 200 includes an outer knob housing 202 and an outer tube 204 extending from a distal end of the knob housing 202. The knob housing 202 and the outer tube 204 are configured and dimensioned to house the components of the adapter 200. The outer tube 204 is dimensioned for endoscopic insertion, in particular, the outer tube 204 is passable through a typical trocar port, cannula, or the like. The knob housing 202 is dimensioned to not enter the trocar port, cannula, or the like. The knob housing 202 is configured and adapted to connect to the connecting portion 104 of the handle housing 102 of the surgical device 100.

Adapter 200 includes a plurality of force/rotation transmitting/converting assemblies disposed therein. Each force/rotation transmitting/converting assembly is configured and adapted to transmit/convert a speed/force of rotation (e.g., increase or decrease) of the first, second and third rotatable drive connectors 106, 108, 110 of surgical device 100 before transmission of such rotational speed/force to the loading unit 300.

Adapter 200 further includes an attachment/detachment button 214 supported thereon. Specifically, the button 214 is supported on the drive coupling assembly 212 of the adapter 200 and is biased to an un-actuated condition. The button 214 includes at least one lip or ledge 214a formed therewith that is configured to snap behind a corresponding lip or ledge 104b defined along the recess 104a of the connecting portion 104 of the surgical device 100. In use, when the adapter 200 is connected to the surgical device 100, the lip 214a of the button 214 is disposed behind the lip 104b of the connecting portion 104 of the surgical device 100 to secure and retain the adapter 200 and the surgical device 100 with one another. In order to permit disconnection of the adapter 200 and the surgical device 100 from one another, the button 214 is depresses or actuated, against its bias condition, to disengage the lip 214a of the button 214 and the lip 104b of the connecting portion 104 of the surgical device 100.

The adapter 200 includes an electrical assembly 216 supported on and in outer knob housing 202. Electrical assembly 216 includes a plurality of electrical contact pins 218, supported on a circuit board (not shown), for electrical connection to a corresponding electrical plug 112 disposed in the connecting portion 104 of the surgical device 100. The electrical assembly 216 serves to allow for calibration and communication of life-cycle information to the circuit board of surgical device 100 via the electrical plug 112 that are electrically connected to the circuit board (not shown) of surgical device 100.

For a detailed description of the construction and operation of exemplary electromechanical, hand-held, powered surgical instruments 100, adapters 200, and end effectors 300, reference may be made to International Application No. PCT/US2008/077249, filed Sep. 22, 2008 (Inter. Pub. No. WO 2009/039506), U.S. Patent Publication No. 2009/0314821, filed on Aug. 31, 2009, U.S. patent application Ser. No. 12/622,827, filed on Nov. 20, 2009, U.S. patent application Ser. No. 13/875,571, filed on May 2, 2013, and U.S. Provisional Patent Application Ser. No. 61/911,774, filed on Dec. 4, 2013, the entire contents of each of which are incorporated herein by reference.

Figure 3A:
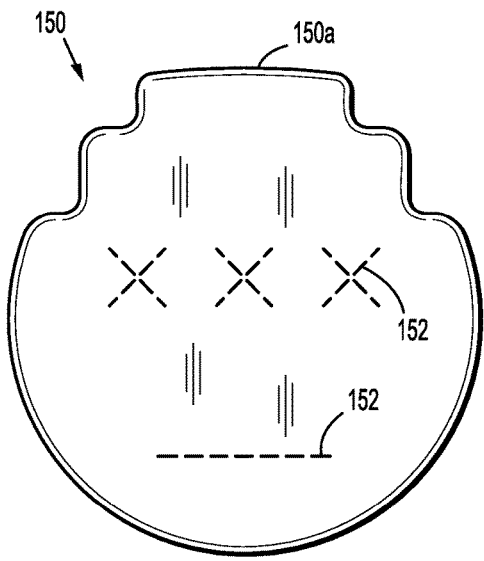
FIGS. 3A and 3B are front views of filters in accordance with embodiments of the present disclosure that are positionable within a distal facing recess of the electromechanical surgical device of FIG. 2.
Figure 3B:
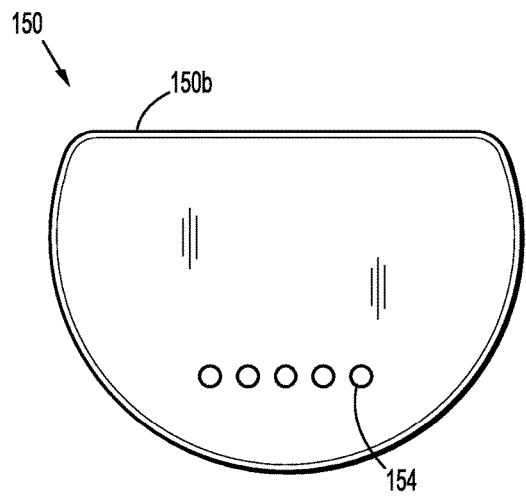

As illustrated in FIGS. 3A and 3B, in conjunction with FIGS. 1 and 2, a filter 150 is removably positionable within the recess 104a of the surgical device 100. The filter 150 protects the electrical components disposed within the housing handle 102 of the surgical device 100 from contaminants on an adapter 200 and/or loading unit 300. In embodiments, shown for example in FIG. 3A, a filter 150a may include an outer dimension or profile that is substantially the same as an inner dimension or profile defined by sidewalls 104c of the recess 104a of the surgical device 100. In other embodiments, as shown for example in FIG. 3B, a filter 150b may be dimensioned to fit within only a portion of the recess 104a.

The filter 150 may include slits 152 (FIG. 3A) or apertures 154 (FIG. 3B) dimensioned to permit reception and passage of an electrical component, such as an electrical contact pin 218 of the adapter 200 therethrough. The slits 152 or apertures 154 may have a small diameter orifice which effectively lowers the insertion pressure needed to insert the electrical contact pin 218 therethrough yet is penetrable to allow the electrical contact pin 218 to contact the electrical assembly 112 of the surgical device 100. The slits 152 may include single or multiple intersecting slits formed within the filter 150 to assist in reducing the insertion forces needed to advance the electrical contact pins 218 into the surgical device 100. In particular, the slits 152 open to permit passage of the electrical contact pin 218, whereby the internal wall portions defining the slit 218 engage the outer surface of the electrical contact pin 218 and wipes contaminants, or disinfects, the electrical contact pin 218 prior to the electrical contact pin 218 contacting the internal electrical components of the surgical device 100 via the electrical plug 112. The slit may be adapted to assume a substantially closed position upon removal of the electrical contact pin 218 therefrom. In some embodiments, the outer dimension of the filter 150 is slightly larger than the inner dimension of the recess 104a so that the slits 152 or apertures 154 are closed upon radial and axial compression of the filter 150 within the recess 104a in the presence or absence of an electrical contact pin 218. Similarly, slits 152 or apertures 154 may be disposed within the filter 150 between the rotatable drive connectors 106, 108, 110 and the rotatable connector sleeve 206, 208, 210.

The filter 150 may be fabricated from a variety of materials. In embodiments, the filter 150 may be a woven, knitted, braided, or non-woven fabric of natural or synthetic materials. In embodiments, the fabric may be densely or tightly configured and/or include more than one layer to form a composite of fabrics. Suitable yarns and fabric materials include synthetic materials such as spandex including, for example, LYCRA® fibers commercially available from Invista North America S.A.R.L., nylon, aramid including, for example, Kevlar® fibers commercially available from E. I. DuPont de Nemours and Company, and other materials that will expand and compress about an electrical contact pin 218 as it is inserted through the filter 150 while providing rigidity and support to the filter 150.

In some embodiments, the filter 150 may be fabricated from an open or closed cell foam material. Foam materials may have sufficient elasticity to bend and conform to the outer dimension of an inserted electrical contact pin 218. Moreover, the compliant characteristics of a foam may substantially minimize the formation of a gap around the electrical contact pin 218 during attachment/detachment of the adapter 200 from the surgical device 100 to ensure a sterile connection.

In embodiments, the filter 150 may be fabricated from elastomers or thermoplastic materials. Suitable elastomers include, for example, polyisoprene, polychloroprene, polyester, polyurethane, polyether urethane, polyvinyl chloride, ethylene vinyl acetate, polybutadiene, polyether block amide, styrene block copolymer, ethylene propylene diene M-class rubber, nitrile rubber, butyl rubber, natural rubber, silicone, and copolymers and combinations thereof.

In some embodiments, the filter 150 may be fabricated from a gel. The gel may be fabricated from an elastomer such as a soft urethane gel, silicone gel, etc., and may have compressible characteristics to permit passage of an electrical contact pin 218 through the filter 150 and to close upon removal of the electrical contact pin 218 from the filter 150. The gel may be a hydrogel or water-containing gel include water and various polymeric substances including, for example, gelatin, polysaccharides, crosslinked acrylamide polymers, hydroxyethylmethacrylate polymers, crosslinked polyhydroxyethylaciylate, polymerized, crosslinked 2-acrylamido-2-methylpropane sulfonic acid polymers or one of their salts, crosslinked polyvinylpyrrolidone, polyacrylic acid, copolymers of the aforementioned monomers with each other, copolymers of the aforementioned monomers with other polymers such as polystyrene or other non-hydrogel forming polymers, one or more salts of the foregoing, and combinations thereof.

It should be understood that the filter 150 may include one or more layers of the same or different materials. For example, in embodiments, the filter 150 may include a first layer, such as a gel or elastomeric layer, and a second layer, which is harder than the first layer, such as a fabric or foam layer, mounted to or embedded within the first layer. The combination of materials of varying hardness aids in retaining the filter 150 within the recess of the surgical device 100 in a self-supporting manner.

The filter 150 may include a therapeutic or pharmacological agent, or combinations thereof, such as antimicrobials, antibacterials, antiseptics, astringents, and disinfectants. In some embodiments, the filter may be placed moistened prior to positioning the filter 150 within the recess 104a of the surgical device 100, such as by placing the filter 150 in an astringent bath.

Figure 4:
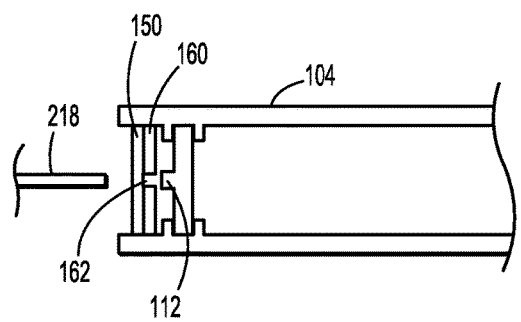
FIG. 4 is a schematic, cross-sectional side view of a filter positioned within an electromechanical surgical device in accordance with another embodiment of the present disclosure.

In an alternate embodiment, as shown in FIG. 4, a filter 150 may be attached to a base plate 160 mounted within the connecting portion 104 of the surgical device 100 distal to the rotatable drive connectors 106, 108, 110 and the electrical plug 112. In embodiments, the base plate 160 may be fixed within the recess 104a. In such embodiments, the filter 150 may be a hydrogel including adhesive properties to support attachment and removal of the filter 150 with the base plate 160. In other embodiments, the base plate 160 may be releasably mounted within the recess 104a, and the filter 150 may be secured to the base plate 160 through conventional means, e.g., with the use of adhesives or molding. The base plate 160 may be formed from a material, e.g., an elastomer, having a greater rigidity than the material of the filter 150, and may include openings 162 that are positioned and dimensioned to correspond with the electrical contact pins 218 of the adapter 200 to permit passage of the electrical contact pins 218 therethrough.

To use the electromechanical surgical assembly, a filter 150 is positioned within the distal facing recess 104a of the connecting portion 104 of the surgical device 100. In embodiments, prior to positioning the filter within the recess 104a, the filter 150 may be moistened with a therapeutic agent. Next, the adapter 200 is connected to the surgical device 100 by positioning the proximal facing cap 212a of the drive coupling assembly 212 within the recess 104a of the connecting portion 104 such that the lip 214a of the button 214 is disposed behind the lip 104a of the connecting portion 104, as described above. When mated, the electrical contact pins 218 protrude proximal of the adapter 200 and pass through the filter 150 prior to contacting the electrical assembly 112. After use, the adapter 200 may be detached from the surgical device 100 by depressing the button 214, and the filter 150 may be removed. A new filter can be positioned within the recess 104a of the connecting portion 104 and the adapter 200 can be re-attached, or a different adapter can be attached, to the surgical device 100 as needed during a single surgical procedure without risk of contamination of the internal components of the surgical device 100.

It will be understood that various modifications may be made to the embodiments of the presently disclosed electromechanical surgical assembly systems. Therefore, the above description should not be construed as limiting, but merely as exemplifications of embodiments. Those skilled in the art will envision other modifications within the scope and spirit of the present disclosure.

What is claimed is:

1. An electromechanical surgical assembly comprising:
    a surgical device including a connecting portion having a distal facing recess including an electrical plug;
    an adapter including a proximal facing cap configured to mate with the recess of the surgical device, the proximal facing cap including an electronic assembly including a plurality of electrical contact pins configured for electrical connection with the electrical plug; and
    a filter removably positioned within the recess of the surgical device, wherein the plurality of electrical contact pins extend through the filter when the adapter is connected to the surgical device.

2. The electromechanical surgical assembly of claim 1, wherein the filter includes at least one layer of material selected from the group consisting of fabrics, foams, elastomers, thermoplastics, gels, and combinations thereof.

3. The electromechanical surgical assembly of claim 2, wherein the filter is composite of two or more layers of material.

4. The electromechanical surgical assembly of claim 1, wherein the filter includes a therapeutic agent.

5. The electromechanical surgical assembly of claim 4, wherein the therapeutic agent is selected from the group consisting of antimicrobials, antibacterials, antiseptics, astringents, disinfectants, and combinations thereof.

6. The electromechanical surgical assembly of claim 1, wherein the filter has a shape complementary to a shape of the recess.

7. The electromechanical surgical assembly of claim 1, wherein the filter includes slits.

8. The electromechanical surgical assembly of claim 1, wherein the filter is self-supporting.

9. The electromechanical surgical assembly of claim 1, wherein the filter is attached to a base plate mounted within the recess.

10. An electromechanical surgical device interconnectable with an adapter for selectively interconnecting a surgical loading unit with the surgical device, the surgical device comprising:
    a handle housing;
    a connecting portion extending distally from the handle housing, the connecting portion including at least one rotatable drive shaft and an electrical plug defined within a distal facing recess; and a filter disposed within the recess distal to the at least one rotatable drive shaft and the electric plug, the filter configured to prevent contaminants from communicating with the electrical plug.

11. The electromechanical surgical device of claim 10, wherein the filter includes at least one layer of material selected from the group consisting of fabrics, foams, elastomers, thermoplastics, gels, and combinations thereof.

12. The electromechanical surgical device of claim 11, wherein the filter is composite of two or more layers of material.

13. The electromechanical surgical device of claim 10, wherein the filter includes a therapeutic agent.

14. The electromechanical surgical device of claim 13, wherein the therapeutic agent is selected from the group consisting of antimicrobials, antibacterials, antiseptics, astringents, disinfectants, and combinations thereof.

15. The electromechanical surgical device of claim 10, wherein the filter has a shape complementary to a shape of the recess.

16. The electromechanical surgical device of claim 10, wherein the filter includes slits.

17. The electromechanical surgical device of claim 10, wherein the filter is self-supporting.

18. The electromechanical surgical device of claim 10, wherein the filter is attached to a base plate mounted within the recess.

19. A method of using an electromechanical surgical assembly, the method comprising:

positioning a filter within a distal facing recess of a connecting portion of a surgical device, the distal facing recess including an electrical plug; and connecting an adapter to the surgical device, the adapter including a proximal facing cap configured to mate with the distal facing recess, the proximal facing cap including an electronic assembly including a plurality of electrical contact pins configured to extend through the filter for electrical connection with the electrical plug.

20. The method of claim 19, further comprising the step of moistening the filter with a therapeutic agent prior to positioning the filter within the distal facing recess of the connecting portion of the surgical device.

21. The method of claim 19, further comprising the steps of:

disconnecting the adapter from the surgical device; and removing the filter from the recess of the surgical device.

22. The method of claim 21, further comprising the steps of:

positioning a new filter within the distal facing recess of the surgical device; and attaching the adapter or a different adapter to the surgical device.

23. The method of claim 19, wherein the step of positioning the filter within the distal facing recess of the connecting portion of the surgical device includes attaching the filter to a base plate mounted within the recess.

* * * * *